United States Patent

Fleckenstein

[11] Patent Number: 5,891,100
[45] Date of Patent: Apr. 6, 1999

[54] SECURING DEVICE FOR BRAIN SCAN PROBES

[76] Inventor: Wolfgang Fleckenstein, Eiderweg 14, 24247 Mielkendorf, Germany

[21] Appl. No.: 860,704
[22] PCT Filed: Jan. 17, 1996
[86] PCT No.: PCT/EP96/00178
    § 371 Date: Jul. 17, 1997
    § 102(e) Date: Jul. 17, 1997
[87] PCT Pub. No.: WO96/22798
    PCT Pub. Date: Aug. 1, 1996

[30] Foreign Application Priority Data

Jan. 25, 1995 [DE] Germany ............ 195 02 183.5

[51] Int. Cl.$^6$ ........................... A61M 25/02
[52] U.S. Cl. ............... 604/175; 604/283; 606/130
[58] Field of Search ............... 604/174, 175, 604/178, 283; 606/129, 130

[56] References Cited

U.S. PATENT DOCUMENTS 4,903,707  2/1990  Knute et al. ............... 128/748
5,112,312  5/1992  Luther ..................... 604/177

FOREIGN PATENT DOCUMENTS

WO 91/12765  9/1991  WIPO.

Primary Examiner—Corrine M. McDermott
Attorney, Agent, or Firm—Walter C. Farley

[57] ABSTRACT

A device for inserting holding and sealing a brain scan probe in a cranial opening has a screw in the cranial opening, an insertion catheter with a probe therein extending through a bore in the screw and a pinch seal in the screw for hermetically sealing the probe in the catheter when it is in position. A protection tube surrounds the catheter and is attached distally to the screw and proximally to a coupling connector. The insertion catheter has an opening which permits longitudinal adjustment of the insertion catheter along the probe and permits introduction of the probe into the catheter and longitudinal movement of the probe.

5 Claims, 1 Drawing Sheet

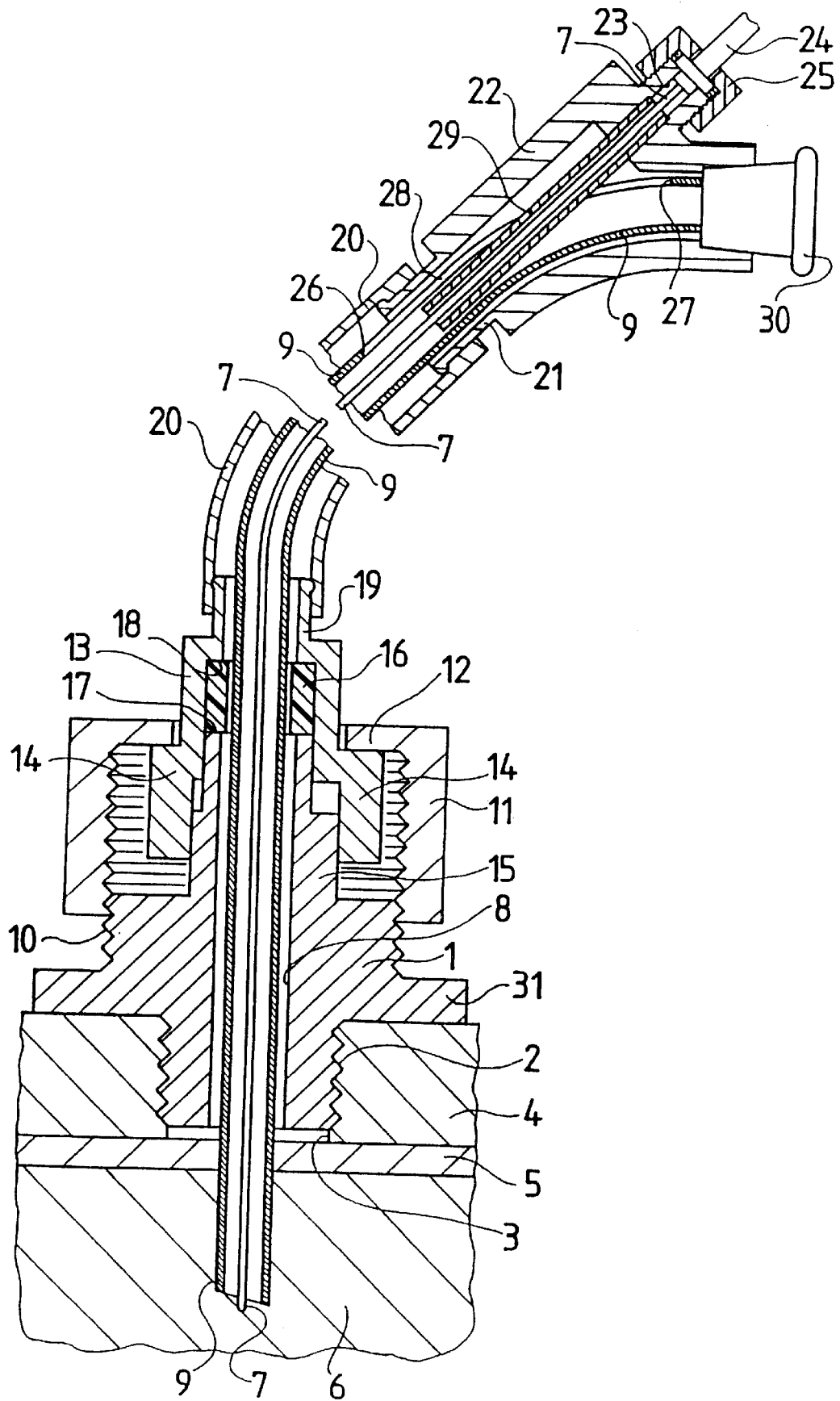

SECURING DEVICE FOR BRAIN SCAN PROBES

FIELD OF THE INVENTION

This invention relates to a device for holding and sealing a brain scan probe threaded into a cranial opening and forming a seal with the opening.

BACKGROUND OF THE INVENTION

A device of this kind is known from the brochure

"Camino Neurosurgical Products" of Messrs Camino Laboratories, San Diego, Calif., U.S.A.

Inside page 1:

The Camino ICP Monitoring KIT.

The device shown serves for the insertion of a probe in the form of a catheter which measures the brain pressure in the tissue and which, after a screw has been fixed in the cranial perforation, is inserted through the protective flexible tube and the screw passage bore into the brain tissue to the required scanning depth. The probe in this known construction has an adequate natural rigidity to enable it to be advanced while being aimed toward the target without any deviations in the direction predetermined by the passage bore. When the insertion position is reached, the probe is fixed on the screw by a pinch seal, with sterile closure of the passage bore. In this construction, the protective flexible tube provides only protective action against lateral incursions on the probe. An electric coupling plug provided at the proximal end of the probe is rigidly connected only to the probe, which in the known construction has sufficient resistance to tension.

The known device offers the possibility of providing a patient with a brain probe over a relatively long period, the brain being protected against infection and the external part of the probe being movable arbitrarily, for example in the event of the patient's shifting, without any risk of electrical malfunction.

There has long been the need to carry out long-term measurements of the tissue pO2, i.e., the oxygen partial pressure in the tissue, in the brain. Probes in the form of catheters suitable for the purpose are available, e.g. Clark type oxygen measuring probes. Probes of this kind suitable for use in brain tissue, however, must be extraordinarily thin and highly flexible, since otherwise they cannot follow the tissue movements during the natural movements of the brain (respiration, pulse beat) and they would injure the tissue. On the one hand, injuries of this kind are harmful to the brain and on the other hand they falsify the oxygen measurement.

With known devices it is not possible to introduce such probes into the brain tissue, since they do not have sufficient natural rigidity for progress into the brain tissue and because they are not sufficiently tension-resistant, so that they would break between the coupling plug and the screw in the event of movements by the patient or manipulation being carried out on the patient.

SUMMARY OF THE INVENTION

An object of the present invention, therefore, is to provide a device of the kind referred to in the preamble of use for oxygen probes suitable in brain tissue.

The highly flexible pO2 probe offers the advantage of enabling the oxygen pressure in the brain tissue to be measured, and in fact without injury to the brain tissue or falsification of the measurement by such injuries. Once the probe has been placed in the tissue, it can passively follow all the movements of the brain tissue. To introduce the probe into the brain tissue, an insertion catheter is provided, which is of sufficient natural rigidity or which is kept naturally rigid during insertion by means of a guide wire, the insertion catheter surrounding the probe during the advance and guiding it in the required direction. From its proximal end, the insertion catheter must be displaceable independently of the probe for the purpose of insertion or subsequent withdrawal with the probe being released in the brain. The known pinch seal directly between the screw and the probe cannot therefore be used. On the contrary, the pinch seal seals on the insertion catheter and, with this, which for this purpose is selected from suitable material, on the probe. An electric coupling plug provided at the proximal end of the probe is connected to the screw in tension-resistant relationship via the protective flexible tube so that breaking away of the extremely sensitive probe is precluded in the event of manipulation at the measuring instruments or in the event of movements of the patient. In this way, an easily handled device, which is reliable in terms of measuring technology and also for the patient, is created by means of which the oxygen partial pressure, which is important for many diagnostic purposes, can be measured without injury in the brain tissue.

Manipulation of the pinch seal is significantly simplified and facilitated by providing a slidable sleeve containing a chamber for the annular pinch seal, the sleeve being clamped axially against the screw by a clamping device, thereby pinching the pinch seal. Security against rotation ensures that no rotary forces are exerted on the insertion catheter during tensioning of the pinch seal so that the insertion catheter does not perform any rotary movement which would damage the brain tissue. The tensioning device can therefore advantageously be in the form of a simple screw cap.

By providing an end piece for releasably holding the proximal portion of the protective flexible tube, and holding the insertion catheter, the end piece facilitates the operating steps at the proximal end of the protective flexible tube. The probe, which is supplied separately for reasons associated with measuring technology, can be introduced from this end and then be fixed to the electric coupling plug. The axial securing of the insertion catheter in its inserted position enables the catheter to be reliably inserted into the brain without it being able to yield axially.

By providing a guide wire during the insertion process, the insertion catheter can be stiffened during insertion into the brain tissue, even if the catheter itself does not consist of sufficiently naturally rigid material.

Through a longitudinal slot near the proximal end of the insertion catheter, a rigid tube holds the probe and permits axial movement of the insertion catheter while leaving the protective flexible tube uninterrupted.

This way it is possible to move the insertion catheter at the proximal end of the protective flexible tube laterally separately from the probe. This facilitates manipulation and the protective flexible tube can be made closed throughout.

BRIEF DESCRIPTION OF THE DRAWING

The invention is illustrated by way of example and diagrammatically in the drawing, in an axial section (not true-to-scale) through a securing device.

DESCRIPTION OF PREFERRED EMBODIMENT

The drawing shows a screw 1, the distal external screwthread 2 of which is screwed into a cranial perforation 3 in the cranial bone 4 of a patient. The dura 5 and brain tissue 6 are shown beneath the cranial bone 4.

A probe 7 in the form of a catheter is advanced into the brain tissue 6 to the depth shown, through a passage bore 8 in the screw 1, and through the dura 5 which is punctured at this place. The probe 7 has a measuring site in the region of the point. In the illustration, which shows an intermediate step in the insertion process, the probe 7 is surrounded, over the entire length into the brain tissue 6, by an insertion catheter 9, formed as a flexible tube of suitable material.

A screw cap 11 engages over an external thread 10 at the proximal end of the screw 1 and engages by an inner flange 12 over a step surface of a sleeve 13 and thus, when the screw is actuated, pulls the sleeve 13 against the screw 1. By means of a sliding guide 14, which is asymmetrical in cross-section and which therefore has a rotation-inhibiting effect, the sleeve engages over a corresponding neck 15 of the screw 1 and is thus slidable thereon in the axial direction while being secured against rotation. At its proximal end, the sleeve 13 forms an annular chamber which surrounds a pinch seal 16 formed as a length of flexible tube, the annular chamber being defined, at its periphery, by a peripheral surface formed by a sleeve 13, and, at the ends, by the end face 17 of the screw 1 and the end face 18 of the sleeve 13.

If the screw cap 11 is screwed further on to the external screwthread 10 of the screw 1, from the initial position shown, the sleeve 13 pulls against the screw 1 with axial shortening of the distance between the end faces 17 and 18. The pinch seal 16, which cannot move outwardly, is thus internally pinched.

Preferably, the material of the pinch seal 16 is somewhat harder than that of the insertion catheter 9, so that a tension-resistant and, in particular, sterile hermetic seal is created between the screw 1 and insertion catheter 9, on the one hand, and the latter and the probe 7, on the other hand.

At its proximal end, the sleeve 13 bears a spigot 19 for the tension-resistant fixing of a protective flexible tube 20 surrounding the insertion catheter 9.

At its proximal end, while still surrounding the insertion catheter 9 with the probe 7 extending therein, the protective flexible tube 20 is fixed on a spigot 21 of an end piece 22, which forms a coupling connector and through which the probe 7 extends to the exterior in a bore 23. At the outer end of the bore 23 the probe 7 is fixed to its electric coupling plug 24, which is releasably fixed to the end piece 22 by a screw cap 25.

In a proximal end zone between the locations 26 and 27, the insertion catheter 9 is provided with a longitudinal slot 28, through which extends a rigid length of tubing 29, which is fixed in the bore 23 in the end piece 22. A grip 30 is fixed at the proximal end of the insertion catheter 9 and can be releasably fixed by its conical outer surface in a conical opening in the end piece 22.

The device illustrated is manipulated in the manner described hereinafter.

The device illustrated is supplied pre-assembled in the position illustrated, without the probe 7. The probe 7 is preferably packed separately, e.g. in a wet pack, which is adapted to prevent drying out of the electrolyte in a probe of the Clark type.

The cranial bone 4 of the patient is prepared so as to be exposed at one point and the cranial perforation 3 is formed. The dura 5 is punctured by a suitable instrument, e.g., a lancet, in the middle of the cranial perforation 3. The screw 1 is then screwed into the position illustrated, for example by means of a spanner engaging over a hexagonal flange 31 of the screw 1.

Instead of the probe 7, a guide wire (not shown) is introduced into the device until it is situated exactly in the position of the probe 7 as illustrated. It is fixed, e.g. clamped on the end piece for the further manipulation.

The device is then attached to the screw 1 in the manner illustrated, the insertion catheter 9 stiffened by the guide wire being advanced through the pre-punctured dura 5 into the brain tissue 6 as far as the position illustrated. The sleeve 13 is placed with its sliding guide 14 on the neck 15 of the screw 1 so as to be secured against rotation and the screw cap 11 is screwed with just a few turns loosely on the external screwthread 10 of the screw 1, initially without pinching the pinch seal 16.

The guide wire is then withdrawn and the probe is inserted to the position shown. It is reliably guided to the required location by the insertion catheter 9. The probe 7 is secured in its axial position by screw cap 25.

The connections between grip 30 and the end piece 22 is then released and the insertion catheter 9 is withdrawn until its distal end is withdrawn from the brain tissue 6, in which only the very thin and flexible probe 7 now lies.

By further screwing on of the screw cap 11 against the screw 1 the pinch seal 16 is then compressed, the said sealing effect being produced.

The electric coupling plug 24 is connected to an electronic measuring instrument (not shown in the drawing) disposed near the patient, and the probe 7 is then ready for operation.

Some variations are possible from with the preferred embodiment illustrated.

For example, the insertion catheter can terminate before the end piece 22 with its proximal end inside the protective flexible tube. In that case, instead of the grip 30, there should be provided at the proximal end of the insertion catheter 9 a grip which can be actuated through a longitudinal slot in the protective flexible tube 20 or in some other way therethrough for the purpose of longitudinal displacement of the insertion catheter. The length of tubing 29 in the end piece 22 can then be dispensed with.

The pinch seal can be actuated in some manner other than that shown, e.g., by means of a lever press or the like engaging from the exterior.

The insertion catheter 9 can be of a material having sufficient natural rigidity to be accurately moveable to the target in the brain tissue even without the insertion wire. This may give rise to certain problems in connection with sealing in the region of the pinch seal 16 in order to ensure damage-free sealing on the probe 7. These problems can be solved by suitable construction of the pinch seal.

I claim:

1. A device for inserting, holding and sterile sealing of a brain scan probe in a cranial opening comprising a screw having an external thread at a distal end thereof adapted to engage the cranial opening, said screw having an axial bore therethrough;

an insertion catheter comprising a hose having an open distal end adapted to receive a brain scan probe therethrough, said catheter extending through said axial bore and being longitudinally movable within said bore;

a pinch seal in said screw adapted to hermetically seal and axially fix said probe in said insertion catheter by pinching said insertion catheter against said probe;

a protection tube attached and axially fixed at a distal end to said screw and surrounding said insertion catheter; and a coupling connector attached to a proximal end of said protection tube for connecting to a proximal end of said probe;

said insertion catheter having an opening therethrough inside said protection tube for permitting longitudinal adjustment of said insertion catheter along said probe and permitting introduction of said probe into said catheter, and said probe being longitudinally movable through said opening.

2. A device according to claim 1 including a slidable sleeve connecting said distal end of said protection tube to said screw, said sleeve having an interior chamber containing said pinch seal and being axially movable to compress and pinch said seal, and a clamping device for axially clamping said sleeve against said screw.

3. A device according to claim 1 including at the proximal end of said coupling connector means for releasably attaching a coupling plug to said probe, and means for axially securing said insertion catheter in an inserted position.

4. A device according to claim 1 and including a guide wire attachable through said catheter during insertion of said device.

5. A device according to claim 1 wherein said opening is formed at a proximal portion of said insertion catheter, said device including a rigid length of tubing attached to a proximal end of said protection tube for entering said opening in all axial positions of said insertion catheter and being adapted to receive said probe and introduce said probe into said insertion catheter through said opening.

* * * * *